(12) United States Patent
Summers

(10) Patent No.: US 6,395,023 B1
(45) Date of Patent: *May 28, 2002

(54) PROSTHESIS WITH BIODEGRADABLE SURFACE COATING AND METHOD FOR MAKING SAME

(75) Inventor: David P. Summers, Montgomery, TX (US)

(73) Assignee: Endovasc Ltd., Inc., Montgomery, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 09/309,949

(22) Filed: May 11, 1999

Related U.S. Application Data

(63) Continuation-in-part of application No. 08/797,743, filed on Feb. 7, 1997, now Pat. No. 5,980,551.

(51) Int. Cl.$^7$ .................................................. A61F 2/06
(52) U.S. Cl. ..................................... 623/1.44; 623/1.46
(58) Field of Search ................................. 606/194, 191, 606/198, 154, 195; 623/1.1, 1.12, 1.39, 1.46, 1.44; 424/450, 424–426

(56) References Cited

U.S. PATENT DOCUMENTS

| | | | | |
|---|---|---|---|---|
| 5,464,450 A | * | 11/1995 | Buscemi et al. | 606/195 |
| 5,575,818 A | * | 11/1996 | Pinchuk | 606/195 |
| 5,674,242 A | * | 10/1997 | Phan et al. | 606/198 |
| 5,788,979 A | * | 8/1998 | Alt et al. | 606/194 |
| 5,876,452 A | * | 3/1999 | Athanasiou et al. | 623/16 |
| 5,980,551 A | * | 11/1999 | Summers et al. | 606/194 |

* cited by examiner

*Primary Examiner*—Kevin Truong
(74) *Attorney, Agent, or Firm*—Nick A. Nichols Jr.

(57) ABSTRACT

A prosthesis for replacing or strengthening a particular part of the body is coated with a biodegradable, resorbable and biocompatible surface coating. Biologically active microspheres which controllably release the biologically active agents are embedded in the surface coating. The biologically active microspheres include encapsulated PGE1 in a polyethylene glycol mix, which over a period of time dissolves and releases the PGE1 into the body part.

9 Claims, 1 Drawing Sheet

PROSTHESIS WITH BIODEGRADABLE SURFACE COATING AND METHOD FOR MAKING SAME

RELATED APPLICATIONS

This application is a continuation-in-part application of U.S. patent application Ser. No. 08/797,743 filed on Feb. 7, 1997 now U.S. Pat. No. 5,980,551.

BACKGROUND OF THE INVENTION

The present invention relates to prosthetic devices, particularly prosthetic devices coated with a biocompatible substance impregnated with pharmacologically active agents released over a period of time to reduce or eliminate restenosis in blood vessels, stimulate bone growth or regeneration of a neoarterial wall.

Prosthetic devices are artificial devices used to replace or strengthen a particular part of the body. Various prosthetic devices are available, such as joint replacement prosthesis, stent prosthesis and vascular graft prosthesis. When implanting a prosthesis, such as a stent prosthesis described in greater detail latter herein, it is desireable that the prosthesis closely assimilate the characteristics of the tissue or bone that the prosthesis is designed to repair or replace. To this end, many attempts have been made to improve biocompatible and mechanical properties of prosthetic devices.

Percutaneous endovascular prosthetic stents were conceived in the late 1970's as a way to prevent both acute occlusion and late restenosis after catheter intervention, but initial clinical results of coronary stenting in 1987 were plagued by high (>20%) acute and subacute thrombosis and were restricted to use as "bailout" for threatened or acute vessel closure. In recent years, stent outcomes have improved progressively with better placement techniques and in 1995, an estimated 700,000 stents were implanted world-wide. Recent STRESS (Stent Restenosis Study, 1994) and BENESTENT trials (Belgium-Netherlands Stent, 1995) demonstrated that stenting of native coronary arteries is associated with greater procedural success. The trials demonstrated that fewer acute, adverse events and less angigraphic restenosis and lower rates of 8-months target vessel revasculerization occurred than in conventional balloon angioplasty. Stents are now used as primary treatment and secondary bailout.

Despite their utility, stents have been plagued by two problems, namely, acute occlusion due to thrombosis and persistent occurrence of restenosis. Recent studies show that coronary stenting results in significant platelet, polymorphonuclear leukocyte, and macrophage activation, as well as activation of the coagulation pathway which induce clots despite passivation and/or anti-coagulation treatment of the stent surface. This limitation relates to the surface exposure of adhesion receptors on activated platelets to the foreign surface of the stent, producing the aforementioned thrombogenic activity that must be countered with intense anticoagulation regimens. Subacute stent thrombosis occurs most frequently during the first few days after implantation and almost always in the first two weeks. Thereafter, neointimal cells including proliferating smooth muscle cells from the vessel wall and endothelial hyperplastic cells encompass the stent surface and ameliate the risk of stent thrombosis.

Notwithstanding the above, vascular stents have proven to be of great therapeutic value in the treatment and prevention of complications relating to percutaneous transminal coronary angioplasty (PTCA). Mechanical problems of the vessel wall, i.e., vesssel dissection, the most frequent cause of acute closure in about 25% of patients leading to acute myocardial infarction associated with PTCA, is virtually eliminated with stents. However, such major acute and chronic adverse events persist in more than 25% of patients. One of the most important causes is the trombogenicity of the stent itself. Despite increased biocompatability curently available, stents have less than hemocompatability and are further limited because of late incidence in virtually all stents of restenosis, potentially fatal late complications from clotting and an aggressive type of in-stent restenosis resistant to therapy. In-stent restenosis is much more difficult to treat than PTCA restenosis, frequently resulting in coronary artery bypass grafting (CABG).

In addition to the morbidity and mortality, stents are more expensive than PTCA and require longer hospitalization in order to provide anticoagulant and antispasm therapy due to the induction of thrombogenicity and spasm by the stent, a foreign object, introduced into the vascular wall. The heavy anticoagulation required can produce major bleeding events and vascular complications, often necessitating surgical intervention.

What is desired is a stent coating of antithrombolic, antispasm agents which will biodegrade over time, eluting drugs into the vessel wall to inhibit these complications and obviating systemic oral or intravenous or intraarterial drug delivery with heightened cost and side effect profile. PGE1 is the ideal antithrombolic agent and antispasmodic agent, which also has antiproliferative effects on the smooth muscle cell (SMC). In addition, PGE1 is very effective in antiplatelet activation and deposition, and produces blocking effects on leukocyte adhesion molecules through the lipoxygenase and leukotriene pathway and blocks macrophage migration and aggregation at the injury site.

Much work has been done to both passivate and/or biologically enhance the surface porperties of stents so as to reduce the need for anticoagulants and the like. For example, Bolz, et al., described a process for coating stents with a semi-conductor (Bolz, A., et al, Coating of Cardiovascular Stents with a Semi-Conductor to Improve Their Hemocompatability, Tex. Heart Inst. Jour. 1996;23:162–6) which provided electrical passivation of the surface charge of stents thereby neutralizing the attraction of coagulating proteins. Other investigations have grafted both active and neutral substances to stents, such as hirudin or neutral collagen, in attempts to ameliate coagulation. (Prietzel, K. et al. Inhibition of Neointimal Proliferation with a Novel Hirudin/Prostacyclin Analog Eluting Stent Coating in an Animal Overstrech Model, Abstract, Circulation, Supplement 1, Vol. 94, No. 8, Oct. 15, 1996, p. 1–260); U.S. Pat. No. 5,342,387, Summers, Artificial Support for a Blood Vessel. These coatings have proven less than successful in ameliating the total problem. Two factors, cellular proliferation within the stent lumen itself and late vessel wall remolding, remain unsolved.

Restenosis within and around the stent is a process of chronic new endothelial and medial cellular growth, and remolding of the vessel after intervention which usually occurs by the third month postintervention. Restenosis is a continuum of extracellular matrix rebuilding after stretching, which continues from the time of PTCA, peaking at three months and unusually terminating after six months. Although percutaneous delivery of stents has been shown to sightly reduce the frequency of restenosis as compared to PTCA, when such lesions do occur within a stent, they have been considered to result from intimal proliferation with smooth muscle cells, the predominate cell type, and are resistant to treatment, since PTCA is generally precluded and rotational atherectomy or CABG usually required. Therefore, it is obvious that stent occlusion is a two-phase problem having an acute phase in which platelet, leukocyte, macrophage aggregation, and thrombosis is the primary concern and a chronic and late-phase problem in which intimal in-stent proliferation and vessel wall remolding is the primary concern. It is, therefore, an object of the instant invention to overcome both acute and chronic concerns with the foregoing invention.

Since most cellular interactions are protein mediated, the prevention or reduction in protein absorption to a stent would serve to prevent cellular attachment and subsequent events that may otherwise render the stent materials biocompatable but in doing so, produce the unwanted adverse effects of not coating the stent. A stent coated with a composition of both biocompatable agents and drug eluting systems such as PGE1 to retard initial harmful vascular cellular and thrombosis mechanisms, while allowing normal subsequent acceptance of the stent by the vessel wall by orderly vascular cell covering with endothelial and medial cells, and compatible treatment for post-PTCA complications would be desirable.

Poly-L-lactic acid (PLLA)/Poly-caprolactone (PCL) blends of aliphatic polyester polymers have proven to be both biodegradable, resorbable and biocompatible. Depending on the ratio of PLLA to PCL, these coatings can provide a benign substrate that provides a microporous structure that can efficiently be impregnated with biologically active microsphere such as liposomes in the range of 20 nm to 1000 nm.

It is therefore an object of the invention to provide a prosthetic device having a PLLA/PCL coating substrate formed thereon and impregnating the coating substrate with biologically active microspheres.

It is a further object of the invention to provide a prosthetic coating whereby the coating substrate is coated with a layer of PGE1-encapsulated liposomes which release PGE1 over an extended period of time.

SUMMARY OF THE INVENTION

The present invention provides a prosthesis coated with a biodegradable, resorbable and biocompatible surface coating. The surface coating is impregnated with biologically active microspheres which controllably release a biologically active agent. The biologically active microspheres include encapsulated PGE1 in a water soluble polyethylene glycol mixture, which over a period of time dissolves and releases the PGE1.

BRIEF DESCRIPTION OF THE DRAWINGS

So that the manner in which the above recited features, advantages and objects of the present invention are attained can be understood in detail, a more particular description of the invention, briefly summarized above, may be had by reference to the embodiments thereof which are illustrated in the appended drawings.

It is noted, however, that the appended drawings illustrate only typical embodiments of this invention and are therefore not to be considered limiting of its scope, for the invention may admit to other equally effective embodiments.

DETAILED DESCRIPTION OF A PREFERRED EMBODIMENT

Figure 1:
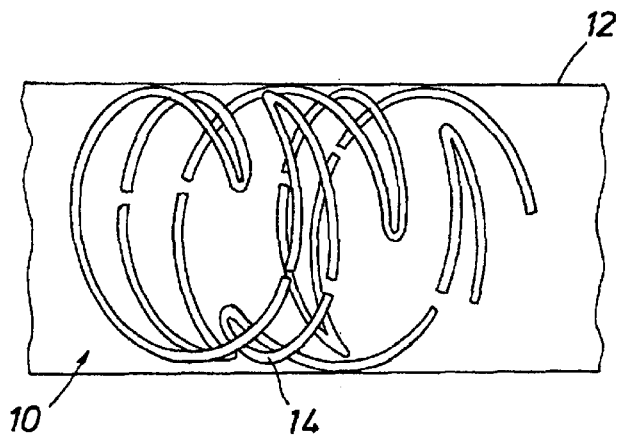
FIG. 1 is an enlarged view of two loops of a double-helix prosthesis according to the invention located within a blood vessel.

Referring first to FIG. 1, a stent prosthesis of the invention, generally identified by the reference numeral 10, is shown located in a blood vessel 12. The stent 10 is shown as having a double-helix wire configuration positioned in a blood vessel for illustrative purposes. Another accepted practice for the treatment of various vascular disorders is a surgical procedure involving the placement of a vascular graft in a patient's vascular system. Typically, vascular grafts are formed from a woven or knotted tubular fabric as well as non-fabric tubes such as expanded polytetrafluoroethylene. It is understood that a vascular graft or stent 10 may comprise various configurations and be positioned in any organ requiring support to open a lumen or passageway without departing from the scope of the present invention.

Referring still to FIG. 1, the stent 10 is located in the vessel 12 in the region where the vessel wall has collapsed and requires support to maintain the vessel 12 in an open condition. While it has been shown that stents have great therapeutic value, stents have suffered from unacceptable hemocompatibility which typically results in restenosis of the vessel 12 which is much more difficult to treat.

Figure 2:
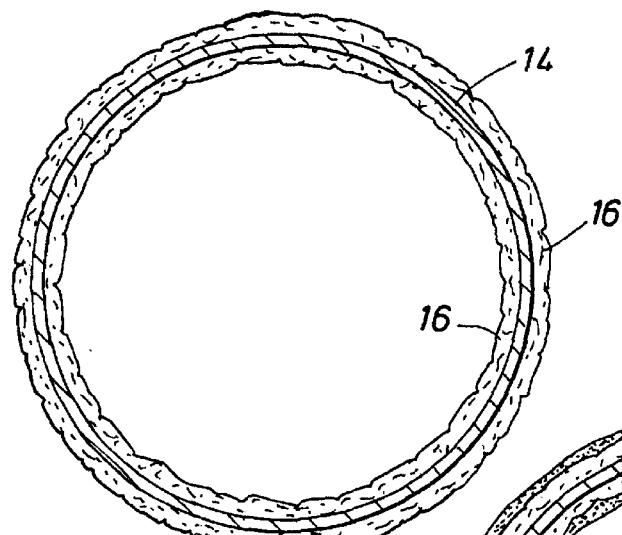
FIG. 2 is a sectional view of a prosthesis of the invention depicting a coating applied on the surface of the prosthesis.
Figure 3:
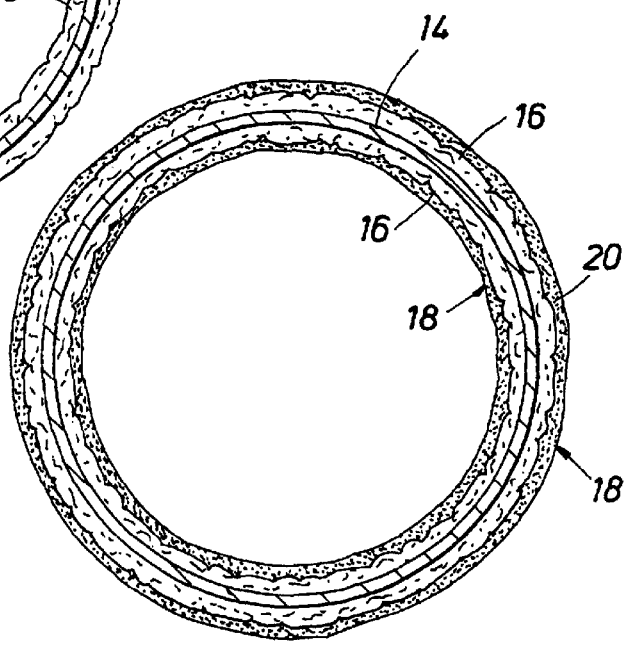
FIG. 3 is a sectional view of a prosthesis of the invention depicting the coating and encapsulated biologically active microspheres applied on the surface of the prosthesis.

Referring now the FIG. 2, stent 10 of the invention comprises a wire 14 which, as noted above, is configured in the shape of a double-helix. The wire 14 is coated with a substrate 16. The substrate 16 encapsulates the stent wire 14 and comprises, in the preferred embodiment, a 50:50 combination of PLLA/PCL which is swollen in 40% trifluoacetic acid with polyethylene oxide (PEO) to first open the pores of the substrate 16 for loading of microspheres or liposomes in microspherical geometries (according to Rajasubramanian, et al, Fabrication of Resorbable Microporous Intravascular Stents For Gene Therapy Applications, ASAIO Journal, 1994, M584–89). The acidic combination etches the skin surface and the pore walls of the substrate 16, rendering the polymer surfaces more hydrophilic. The etched pores 17 of the substrate 16 have an irregular pore surface and define a mean pore size of 150–200 nm long axis and 50–75 nm short axis. The porosity of the substrate 16 is in the range of 19% to 44%.

Figure 4:
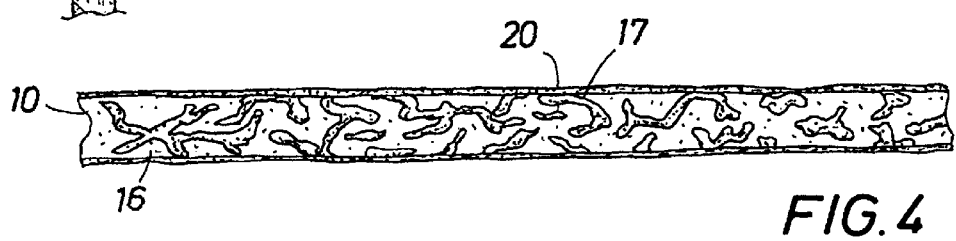
FIG. 4 is an enhanced microscopic view of the prosthesis coating of the invention.

After swelling, the surface of the substrate 16 is coated with a slurry of PGEI-encapsulated liposomes in a polyethylene glycol (PEG) mix 18 having a neutral pH which first fills and then collapses the pores 17 of the substrate 16 about the embedded liposomes 20, as best shown in FIG. 4. The pores 17 are filled with liposomes 20 of 100 nm to 200 nm diameters, providing a mean average of about 1000 liposomal microspheres per pore. What remains then is a modified surface coating, producing biocompatible, cell-non-adhesive surface of PEG and lyophilized liposomal microspheres. PEG itself has been shown to have protein-repelling activity when immobilizing on a surface due to its hydrophilicity, chain mobility, and lack of ionic charge. Since PEG is water-soluble, platelet adhesion and thrombus formation is further limited by a continuous semi-dissolved molecular disassociation which actually increases the hydrophilicity of the-stent substrate 16, making surface adhesion on the stent 10 even more difficult.

After placement of the stent 10 in the vessel 12, the water-soluble surface polymers of PEG begin to dissolve thereby exposing the surface embedded liposomes 20. The liposomes 20 are exposed in stages; the first exposure being those on or close to the surface coating of the substrate 16. The liposomes 20 embedded within the pores 17 of the substrate 16 remain inactivated until both the PEG overlay mixture 18 and the portion of PLLA/PCL encompassing the closed pores 17 of the substrate 16 has been resorbed and thereby releasing the liposomes 20, a process that may continue over a period of time up to six months.

Once the outer coating of the substrate 16 is "dissolved" and upon activation, the liposomes 20 release their biologically active agent by leaking out the liposomes 20 into the vessel wall 12. In the preferred embodiment of the present invention, the active agent encapsulated within the liposomes 20 is prostaglandin E1 (PGE1), a natural-occurring fatty acid of the cyclopentenone family.

The release of the liposomal PGE1 produces a secondary effect that is both synergistic and antagonistic. It is synergistic with the PEG, in that the PEG tends to accumulate at the injured tissue and with long chain lengths further inhibits cellular interactions at the polymer surface, but in addition, the timed release of PEG1 produces powerful chronic antagonistic chemotaxis to thromboxane and leukotriene actions on the platelets and injured vessel wall while modulating the proliferation of smooth muscle cells (SMC) and extracellular matrix within the media of the blood vessel 12. This two-stage process continues to produce inhibition of protein absorption and hence cellular interactions at the biomaterial surface while releasing powerful inhibitions of platelet aggrandizement and modulators of cell growth in the region of the vessel wall 12 where the stent 10 is located. The protein inhibiting action of the biologically active agent continues over a predetermined period of weeks or months or until endothelialization of the biosurface is complete. Of particular note, the labile PEG end-groups on these modified surfaces can be made to serve as attachment sites for suitable biospecific peptides that result in a surface that could potentially adhere to only one particular cell type, such as endothelial cells in the case of stents or vascular grafts.

Figure 5:
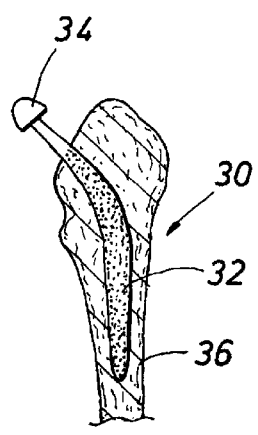
FIG. 5 is a partial sectional view of a hip replacement prosthetic device in accordance with the present invention.

Referring now to FIG. 5, a stem type without cement fixation hip prosthesis 30 is shown. The prosthesis 30 comprises a metal stem 32 which may have a smooth and/or a porous surface. A modular femoral ball 34 is mounted on one end of the stem 32. The stem 32 is a press-fit prosthesis which is implanted in a cavity prepared in the bone 36. The bone cavity is sized to closely approximate the shape of the stem 32. The stem 32 is coated with a PEG mixture 18 in the manner described above. In a process known as porous ingrowth or osseointegration, the bone 36 will attach to the stem 32. Release of PGE in the manner described above stimulates bone growth and hastens and/or enhances bone fixation to the stem 32. The prosthesis 30 shown in FIG. 5 is depicted for illustrative purposes being utilized in as a hip implant. It is understood however that a prosthetic device in accordance to the invention has many applications including, but not limited to, as a knee, shoulder, elbow, ankle, wrist, hand, finger joint, mandibular joint, dental implant or acetabular cup implant prosthesis.

While various embodiments of the invention has been shown and described, it is understood that other and further embodiments of the invention may be devised without departing from the basic scope thereof, and the scope thereof is determined by the claims which follow.

What is claimed is:

1. A prosthetic device comprising a body having a biodegradable coating applied to a surface of said body, said coating releaseably retaining prostaglandin and/or other pharmacological equivalent in said coating.

2. The prosthetic device of claim 1 wherein said substrate comprises one or more layers of a resorbable PLLA/PLC mixture encapsulating said body.

3. The prosthetic device of claim 2 wherein said polymer mixture comprises a slurry of polyethylene glycol (PEG) and liposomes carrying a biologically active agent.

4. The prosthetic device of claim 2 wherein said substrate and said polymer mixture are water soluble and resorbable, providing a continuous and gradual release of prostaglandin encapsulated in said biologically active microspheres.

5. The prosthetic device of claim 1 wherein said substrate comprises Poly-L-lactic acid/Polycaprolactone mixture encapsulating said body, and wherein said polymer mixture comprises a Polyethylene glycol/lyophilized liposome surface coating on said body, and wherein the liposomes in said surface coating range in average diameter from about 100 nm to 200 nm.

6. The prosthetic device of claim 1 wherein the pores of said substrate define an irregular pore surface for releaseably retaining said biologically active microspheres, and wherein said microspheres contain prostaglandin E lencapsulated in said mocrospheres.

7. The prosthetic device of claim 6 wherein the pores of said substrate have a mean pore size of 150 nm to 200 nm long axis and 50 nm to 75 nm short axis.

8. The prosthetic device of claim 7 wherein said microspheres release prostaglandin E1 at a controlled rate for up to six months.

9. The prosthetic device of claim 1 wherein said substrate has a porosity of 18% to 45%.

* * * * *